US012636336B2

(12) United States Patent
Giori et al.

(10) Patent No.: US 12,636,336 B2
(45) Date of Patent: May 26, 2026

(54) **USE OF A VEGETAL EXTRACT FROM *SALVIA HAENKEI* AS AN ACTIVE AGENT IN THE TREATMENT OF A MUSCULOSKELETAL DISORDER**

(71) Applicant: Altergon S.A., Lugano (CH)

(72) Inventors: Andrea Maria Giori, Lugano (CH); Andrea Alimonti, Lugano (CH)

(73) Assignee: IBSA INSTITUT BIOCHIMIQUE SA, Lugano (CH)

( * ) Notice: Subject to any disclaimer, the term of this patent is extended or adjusted under 35 U.S.C. 154(b) by 232 days.

(21) Appl. No.: 18/576,255

(22) PCT Filed: Jul. 1, 2022

(86) PCT No.: PCT/EP2022/068297
§ 371 (c)(1),
(2) Date: Jan. 3, 2024

(87) PCT Pub. No.: WO2023/280717
PCT Pub. Date: Jan. 12, 2023

(65) Prior Publication Data
US 2024/0285711 A1 Aug. 29, 2024

(30) Foreign Application Priority Data
Jul. 5, 2021 (IT) ........................ 102021000017678

(51) Int. Cl.
| | |
|---|---|
| *A61K 36/00* | (2006.01) |
| *A61K 36/537* | (2006.01) |
| *A61P 19/00* | (2006.01) |
| *A61P 19/02* | (2006.01) |
| *A61P 21/00* | (2006.01) |

(52) U.S. Cl.
CPC ............ *A61K 36/537* (2013.01); *A61P 19/00* (2018.01); *A61P 19/02* (2018.01); *A61P 21/00* (2018.01); *A61K 2236/333* (2013.01); *A61K 2236/39* (2013.01); *A61K 2236/51* (2013.01)

(58) Field of Classification Search
CPC .................................................... A61K 36/537
See application file for complete search history.

(56) References Cited

U.S. PATENT DOCUMENTS

2016/0106661 A1* 4/2016 Alimonti .............. A61K 36/537
424/746

FOREIGN PATENT DOCUMENTS

| EP | 2762131 A1 | 8/2014 | |
|---|---|---|---|
| WO | WO-2019121425 A1 * | 6/2019 | ............. A61K 38/39 |

OTHER PUBLICATIONS

Search Report and Written Opinion of PCT/EP2022/068297 issued Oct. 6, 2022.

* cited by examiner

*Primary Examiner* — Qiuwen Mi
(74) *Attorney, Agent, or Firm* — Silvia Salvadori, P.C.; Silvia Salvadori

(57) ABSTRACT

The present invention relates to the use of *Salvia haenkei* extract as an active agent in the treatment of musculoskeletal disorders, being able to offer a significant contribution in slowing, relieving, reducing and/or preventing alterations and damages of the musculoskeletal tissues. Furthermore, the present invention also relates to a pharmaceutical composition comprising *Salvia haenkei* extract and suitable pharmaceutically acceptable excipients, for use in the treatment of musculoskeletal disorders.

16 Claims, 5 Drawing Sheets

A

B

USE OF A VEGETAL EXTRACT FROM *SALVIA HAENKEI* AS AN ACTIVE AGENT IN THE TREATMENT OF A MUSCULOSKELETAL DISORDER

This application is a U.S. national stage of PCT/EP2022/068297 filed 1 Jul. 2022, which claims priority to and the benefit of Italian Application No. 102021000017678 filed 5 Jul. 2021, the contents of which are incorporated herein by reference in their entireties.

DESCRIPTION

Field of the Invention

The present invention relates to the use of *Salvia haenkei* extract as an active agent in the treatment of musculoskeletal disorders, such as injury or disorder of the muscles, nerves, tendons, joints, cartilage, and spinal discs. *Salvia haenkei* extract offers a significant contribution in slowing, relieving, reducing and/or preventing alterations and damages of the musculoskeletal system. Furthermore, the present invention also relates to a pharmaceutical composition comprising *Salvia haenkei* extract and suitable pharmaceutically acceptable excipients, for use in the treatment of musculoskeletal disorders.

Background

The term "musculoskeletal disorders", or indifferently "musculoskeletal pathologies", refers to a variety of acute and/or chronic pathologies, that can affect the human body's movement or any of the tissues of the musculoskeletal system, such as muscles, tendons, ligaments, nerves, bones, discs, blood vessels, etc.

Musculoskeletal disorders (MSDs) comprise then several conditions that affect the locomotor system of individuals. They range from those that arise suddenly and are short-lived, such as fractures, sprains and strains, to lifelong conditions associated with ongoing functioning limitations and disability.

Traumatic events can lead to musculoskeletal conditions, as well as adverse drug reactions targeting the musculoskeletal system, in particular further to chemotherapy drugs.

In particular, musculoskeletal conditions affect:

joints, such as arthritis, gout, ankylosing spondylitis;

bones, such as osteoporosis, osteopenia and associated fragility fractures, traumatic fractures;

muscles, such as sarcopenia, muscular inflammation and/or fibrosis;

the spine, such as back and neck pain;

multiple body areas or systems, such as regional and widespread pain disorders and inflammatory diseases such as connective tissue diseases and vasculitis that have musculoskeletal manifestations, for example systemic lupus erythematosus.

Osteopenia is a musculoskeletal disorder characterized by impaired bone mineral density (between −1 and −2.5 standard deviations from the normal mean in a young adult). When bone mineral density is further impaired (below −2.5 standard deviations) there is "osteoporosis". Bone density generally is measured by dual-energy x-ray absorptiometry (DXA). Osteoporosis involves both trabecular and cortical bone. Secondary osteoporosis has an identifiable cause, such as drug treatments, in particular by chemotherapy treatments (e.g. by doxorubicin). Combination treatment involving the concurrent use of radiation and chemotherapy is another treatment regimen with even higher potential for inducing osseous changes.

Bone loss is also typical in chronic inflammatory diseases such as rheumatoid arthritis, psoriasis, ankylosing spondylitis, systemic lupus erythematosus, multiple sclerosis, inflammatory bowel diseases, celiac disease, pemphigus vulgaris, and others. It is also typical in transplantation-related inflammation.

Management of secondary osteoporosis includes the treatment of the underlying disease or administration of calcium, vitamin D or bisphosphonates. However, there is still the need for effective treatments.

Sarcopenia is a syndrome characterized by progressive and generalized loss of skeletal muscle mass and strength (muscle failure) and it is strictly correlated with physical disability, poor quality of life and death.

In clinical practice, case-finding may start when a patient reports symptoms or signs of sarcopenia (i.e., falling, feeling weak, slow walking speed, difficulty rising from a chair or weight loss/muscle wasting).

Sarcopenia can be diagnosed through standardized questionnaires, or by measuring grip strength, calibrated hand-held dynamometer under well-defined test conditions with interpretive data from appropriate reference populations.

Muscle quantity can be reported as total body Skeletal Muscle Mass (SMM), as Appendicular Skeletal Muscle Mass (ASM), or as muscle cross-sectional area of specific muscle groups or body locations. Magnetic resonance imaging (MRI) and computed tomography (CT) are considered to be gold standards for non-invasive assessment of muscle quantity/mass.

Dual-energy X-ray absorptiometry (DXA) is a more widely available instrument to determine muscle quantity (total body lean tissue mass or appendicular skeletal muscle mass) non-invasively, Bioelectrical impedance analysis (BIA) has been explored for estimation of total or ASM. BIA equipment does not measure muscle mass directly, but instead derives an estimate of muscle mass based on whole-body electrical conductivity. Sarcopenia increases the risk of physical limitation and subsequent disability; recent researches also show that this condition increases the risk of comorbid conditions. Sarcopenia can occur secondary to a systemic disease, especially one that may invoke inflammatory processes, e.g., malignancy or organ failure. There is in fact growing interest in effective therapies to counteract the catabolic effect of chronic inflammation. Physical inactivity also contributes to development of sarcopenia, whether due to a sedentary lifestyle or to disease-related immobility or disability. Further, sarcopenia can develop as a result of inadequate intake of energy or protein, which may be due to anorexia, malabsorption, limited access to healthy foods or limited ability to eat. Acute sarcopenia is usually related to an acute illness or injury. Typically, it is treated by means of rehabilitation programs, in the context of a comprehensive treatment, is made up of a nutritional support, exercise, correction of lifestyles, and the use of advanced physical energies. However, there is clear the need for further treatments that take into account the limitations that certain patients can encounter in performing a rehabilitative program. Musculoskeletal conditions affect a large proportion of world population. Also, in general, musculoskeletal conditions are the highest contributor to the global need for rehabilitation, in order to restore functionality of the involved musculoskeletal tissues. Furthermore, they are typically characterized by pain (often persistent) and limitations in mobility, dexterity and overall level of functioning, reducing people's ability to work. Painful conditions require the use of drugs, typically non-steroid anti-inflammatory drugs, cortisone, or even opioids, which can lead to abuse and well-known adverse effects. Therefore, there is still a great need of providing treatments that can treat musculoskeletal disorders by restoring also the musculoskeletal tissues' structure, further than their functionality.

The aim of the present invention is therefore to provide a new effective and non-invasive remedy for the treatment of musculoskeletal disorders, capable of acting at the level of tissues' structure as well as of tissues' functionality.

SUMMARY OF THE INVENTION

Said object has been achieved by the use of *Salvia haenkei* extract as an active agent in the treatment of musculoskeletal disorders, as reported in claim 1.

In another aspect, the present invention relates to a pharmaceutical composition comprising *Salvia haenkei* extract and suitable pharmaceutically acceptable excipients, for use in the treatment of musculoskeletal disorders.

For the purposes of the present invention, said musculoskeletal disorders comprise: osteoporosis, osteopenia, fragility fractures, traumatic fractures, sarcopenia, back and neck pain, bone, muscular or connective tissue inflammations, arthritis, gout, ankylosing spondylitis. Preferably, for the purpose of the present invention said musculoskeletal disorders comprise: osteoporosis, osteopenia, or sarcopenia.

BRIEF DESCRIPTION OF THE FIGURES

The characteristics and the advantages of the present invention will become clear from the following detailed description, the working examples provided for illustrative purposes and the accompanying figures, wherein.

DETAILED DESCRIPTION OF THE INVENTION

Figure 1:
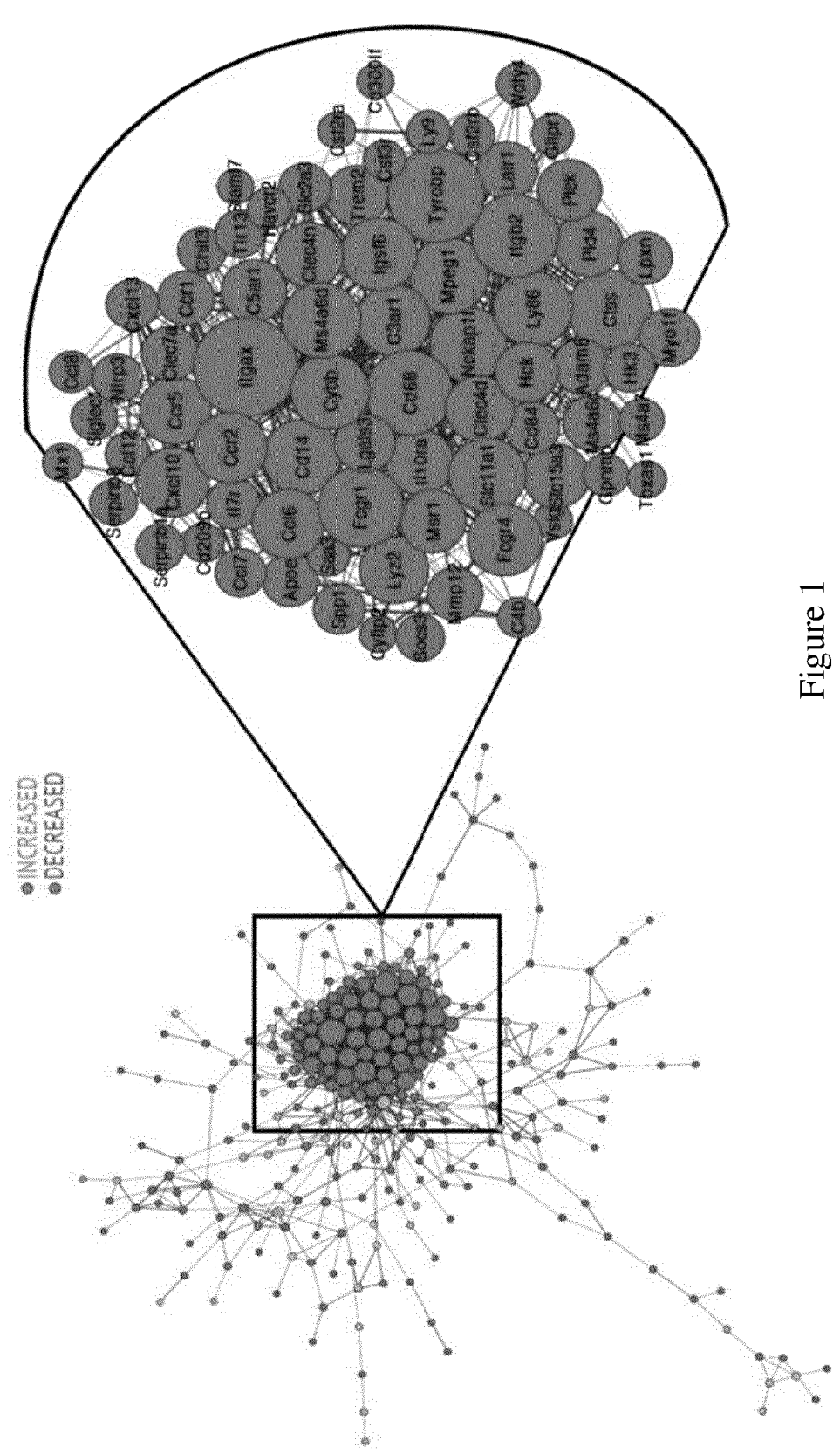
FIG. 1 shows in a representation of the protein-protein interaction network, constructed using the String Database, including differentially expressed genes (FDR<0.05, log 2Fold-change lower than −1 or greater than 1). Nodes' dimension is proportional to the degree of connectivity within the network. Indicated are genes whose expression in the muscle of older mice is significantly increased (in dark grey) or reduced (in light grey). On the right is depicted a close-up view of the most interconnected genes along with their gene symbols.

*Salvia haenkei* is a shrub coming from Bolivia and Peru, commonly called "prawn sage" due to the colour and shape of its shrimp-like flowers. Morphologically, *Salvia haenkei* is characterized by lance-shaped leaves with dentate margins whose length exceeds 12 cm. Their colour is light green and the surface is wrinkled. The inflorescence is very long, over 20 cm and is defined as "raceme", i.e., the flowers are inserted at the level of the central axis through the peduncles of the same length at different heights along the same flower axis.

For the preparation of the extract, the aerial parts of the plant are generally used, i.e., stem, leaves, flowers or mixtures thereof. These parts can be used fresh or after drying under controlled conditions. In both cases, the individual parts or mixtures thereof are contacted with a suitable extraction solvent, by using conventional extraction methods, such as maceration or percolation, or more complex techniques, such as for example extraction with ultrasound, microwaves, pressure or supercritical fluids.

After separation of the exhausted plant, the extract can be used as such, or after substitution of the extractive solvent with one more solvent suitable for human use (such as glycerine or glycol, if not used in the extraction phase). Preferably, the extracting solvent is removed to give a dry extract. For the removal of the extractive solvent, the preferred techniques are evaporation at reduced pressure and low temperature, and atomization.

The extract can also be subjected to subsequent purification steps, to remove potential contaminants (such as lipophilic pesticides), impurities (such as chlorophyll) or to increase the concentration of secondary metabolites.

The so obtained *Salvia haenkei* extract contains a pool of terpenoid compounds, in particular diterpenoids and triterpenoids (Almanza, G. et al., (1997) Clerodane diterpenoids and an ursane triterpenoid from *Salvia haenkei*, Computer-assisted structural elucidation, Tetrahedron, 53 (43), pp. 14719-14728), as well as gallic acid and its derivatives, and chlorogenic acid and its derivatives. Some of these compounds are specific to this species of *Salvia* and differentiate it from other species of the same genus, contributing reasonably to the characteristic activity of its extracts.

The dry extract can be added with suitable excipients, for example to make it smoother, less hygroscopic or standardized in the content of secondary metabolites. Among the excipients that can be used are, for example, silica, maltodextrins, microcrystalline cellulose.

Among the solvents suitable for the preparation of *Salvia haenkei* extract, those with a medium polarity are preferably selected, as being capable of effectively extracting the secondary metabolites of the plant. Preferably, such extraction solvents have a dielectric constant of 8 to 60.

Examples of usable extraction solvents are alcohols having up to 4 carbon atoms, including diols and triols, aldehydes, ketones, organic esters, chlorinated compounds, and mixtures thereof. When miscible, such solvents can also be used in mixture with water.

Preferred solvents include methanol, ethanol, isopropanol, butanol, ethylene glycol, propylene glycol, glycerol, acetone, ethyl acetate and mixtures thereof, as such or mixed with water.

In preferred embodiments, said extraction solvent is a water-alcohol solution, even more preferably it is a 40-80% alcohol solution. Said alcohol is preferably methanol or ethanol. Embodiments in which the extraction solvent is a 60-80% ethanol solution are particularly preferred.

Preferably, the preparation of said *Salvia haenkei* extract comprises the steps of:

1. collecting aerial parts of *Salvia haenkei*,
2. extracting with a solvent, 3. separating the plant exhausted from the liquid extract, and 4. removing the solvent to give the dry extract.

The aerial parts of step 1. may be fresh or preliminarily dried. If the aerial parts are fresh, just harvested, the greater amount of water physiologically present in the plant shall be taken into account.

The invention therefore relates to the use of *Salvia haenkei* extract as active agent for use in the treatment of musculoskeletal disorders.

For the purposes of the present invention, the term "treatment", is meant to include administration of *Salvia haenkei* extract, or of a pharmaceutical composition comprising said extract, to a subject with, or at risk of developing, a musculoskeletal disorder, for the purpose of improving the overall condition of the subject's musculoskeletal tissues, as well as for the purpose of slowing, relieving, reducing, and/or preventing any alteration of the functioning of said tissues in the subject.

Preferably, said musculoskeletal disorders are: osteopenia, osteoporosis, or sarcopenia. These musculoskeletal disorders can be caused by various factors, especially by inflammatory processes, drug treatments, especially by chemotherapy drug. Optionally said musculoskeletal disorders are thus secondary musculoskeletal disorders induced by inflammation or by drugs, such as for example chemotherapy drugs.

In preferred aspects, the *Salvia haenkei* extract is administered in order to improve bones density in the treatment of osteopenia or osteoporosis. Therefore, preferably the *Salvia haenkei* is used as active agent in the treatment of a musculoskeletal disorder by improving bone density.

In further aspects, the *Salvia haenkei* extract is administered for the purpose of slowing, relieving, reducing, and/or preventing inflammation associated with or inducing sarcopenia.

Preferably, said extract is to be administered to a subject in need thereof in a dose of 0.1-1500 mg per day.

In preferred embodiments, said extract is to be administered via systemic route, more preferably by oral administration, in a dose of 1-5000 mg per day, the effective dosage being a function of the extent and severity of the disease to be treated.

Preferably, the daily dose of medicaments is about 1500 mg, preferably from 0.1 to 1000 mg, preferably administered in divided manner about once or 2-3 times a day.

In another aspect, the present invention relates to a pharmaceutical composition comprising *Salvia haenkei* extract and pharmaceutically acceptable carriers, for use in the treatment of musculoskeletal disorders.

In a further aspect, the present invention relates to a food supplement comprising *Salvia* haenkei extract, for use in the treatment of musculoskeletal disorders.

Said pharmaceutical composition or food supplement can be administered via oral route. Optionally, said pharmaceutical composition can be administered topically.

Optionally, the pharmaceutical composition comprises *Salvia haenkei* extract and at least one further active agent, selected from the group consisting of: analgesics, non-steroidal anti-inflammatory drugs (NSAIDs), Muscle relaxants, gabapentinoids, opioids, vitamin D, calcium, myostatin, hormones.

The preparations for oral administration of the pharmaceutical composition comprising the *Salvia haenkei* extract may be in the form of tablets, capsules, soft gelatin capsules, orodispersible film, lozenges, powder, granulate, liquid solutions, dressing, or suspensions. As known in the art, tablets, capsules and lozenges may contain usual excipients in addition to the active ingredient, for example extenders such as lactose, calcium phosphate, sorbitol and the like; lubricants such as magnesium stearate, polyethylene glycol (PEG), binding agents such as polyvinyl pyrrolidone, gelatine, sorbitol, acacia, flavoring agents, disintegrating agents and dispersing agents.

Liquid preparations, generally in the form of aqueous or oily solutions or suspensions, may contain conventional additives such as dispersing agents.

All the pharmaceutical formulations described above can be prepared by methods known in the pharmaceutical technique.

It should be understood that all the aspects identified as preferred and advantageous for the *Salvia haenkei* extract are to be deemed as similarly preferred and advantageous also for the pharmaceutical compositions and uses thereof.

It should be also understood that all the combinations of preferred aspects of the *Salvia* haenkei extract of the invention, as well as of the pharmaceutical compositions and uses of the same, as above reported, are to be deemed as hereby disclosed.

Below are working examples of the present invention provided for non-limiting, illustrative purposes, demonstrating the efficacy of *Salvia haenkei* extracts in the treatment of musculoskeletal disorders.

EXAMPLES

Example 1

Preparation of *Salvia haenkei* Extracts 10 kg of aerial parts of *Salvia haenkei* are harvested from field crops, which are then subjected to a drying process in a ventilated dryer under controlled conditions.

In this way, 1.95 kg of dried plant are obtained, which are minced into a bladed mill to give dried and ground *Salvia* haenkei.

This is used as raw material for the subsequent solvent extractions carried out as described below:

1. 100 g of dried and ground *Salvia haenkei* are introduced into a static percolator and covered completely with 200 ml of a water and ethanol 30-70% v/v mixture. It is left to stand for 2 hours and the extraction solvent (170 ml) is recovered from the bottom of the percolator, which is set aside (extract 1);

2. the humid plant left in the percolator is covered with a new 70% aqueous ethanol (170 ml) aliquot, leaving it to rest for 2 hours. The solvent is recovered (165 ml—extract 2);

3. the extraction described in point 2 is repeated until the dry residue of the extract recovered is less than 5% of the total dry residue extracted up to that moment. At that point, the extraction is considered completed and the spent moist plant is eliminated. 6 extractions are required;

4. the extracts obtained from the individual extraction steps (from extract 1 to extract 6) are combined, filtered and concentrated in a rotary evaporator under vacuum, at a low temperature. It is proceeded until a concentrated, viscous solution (35 ml) is obtained;

5. the concentrated extract is transferred to a steel tray and inserted into a under vacuum cabinet dryer, with heating set at 30° C. After 12 hours, the solvent is completely removed (extract weight loss less than 10%, i.e., dry residue higher than 90%). 14.3 g of integral dry extract are obtained. The ratio drug:extract (DER) is 7:1 (extract 1A).

6. the dried extract obtained is added with 10 g of maltodextrin (DE 10) to improve its consistency and the mixture is milled and sieved, thus obtaining 23.7 g of ground dry extract.

By applying the same procedure but different extracting solvents different native dry extracts were prepared.

The table summarizes the results of the various extractions:

| extract | extraction solvent | DER |
|---------|--------------------|-----|
| 1A | ethanol:water 70:30 | 7:1 |
| 1B | ethanol:water 95:5 | 9.5:1 |
| 1C | acetone | 11:1 |
| 1D | methanol | 8:1 |
| 1E | ethyl acetate | 15:1 |
| 1F | water | 5:1 |
| 1G | methanol:water 50:50 | 6:1 |

In the following Examples, a hydroalcoholic extract of *Salvia haenkei* of Example 1A was used, briefly referred to as "SH".

Example 2

In Vivo Evaluation of SH on Skeletal Muscles

Total mRNA was extracted from the gastrocnemius of: 10 mice at 24 months of age, treated with SH for 4 months, 10 untreated mice at the same age, and 8 mice at 3 months of age. In each group mice were half male and half females. RNAseq was then performed. In order to determine a set of genes whose expression is potentially altered in pathological conditions of the muscular tissue, a differential expression analysis was first performed on muscle-specific transcriptomes of 3 months-old mice compared to those of 24 months-old animals using DESeq2.

Features showing a log 2FoldChange greater than 1 or lower than −1 were selected, to build two signatures, "MOUSE_ADULT_UP" ("increased" in FIG. 1) and "MOUSE_ADULT_DOWN" ("decreased in FIG. 1), consisting of 338 and 109 genes respectively, whose expression changed in 24 months old adult mice compared to 3 months old mice (FIG. 1). These signatures are indeed characterized by genes involved in fibrosis, inflammation, and mitochondrial function.

Figure 2:
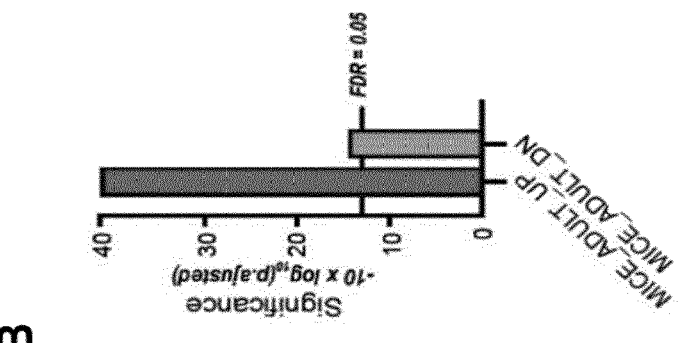
FIG. 2 shows: (A) a representation of the protein-protein interaction network including differentially expressed genes of FIG. 1, wherein grey scale is representative of the log 2Fold-change as determined in Example 2 between SH-treated animals versus aged-matched controls; (B) a barplot representing gene-set enrichment analysis results between SH-treated animals and age-matched controls.

Then transcriptional perturbations occurring in SH-treated mice compared to age-matched adult controls was verified, focusing on the previously identified gene-sets. Both custom derived gene-sets (MOUSE_ADULT_UP/MOUSE_ADULT_DN) tested significant, showing in particular that SH treatment is capable of downregulating genes involved in extracellular matrix remodeling (involved in fibrosis) and inflammation (FIG. 2).

Example 3

SH Effects on Bone and Joint Health

Figure 3:
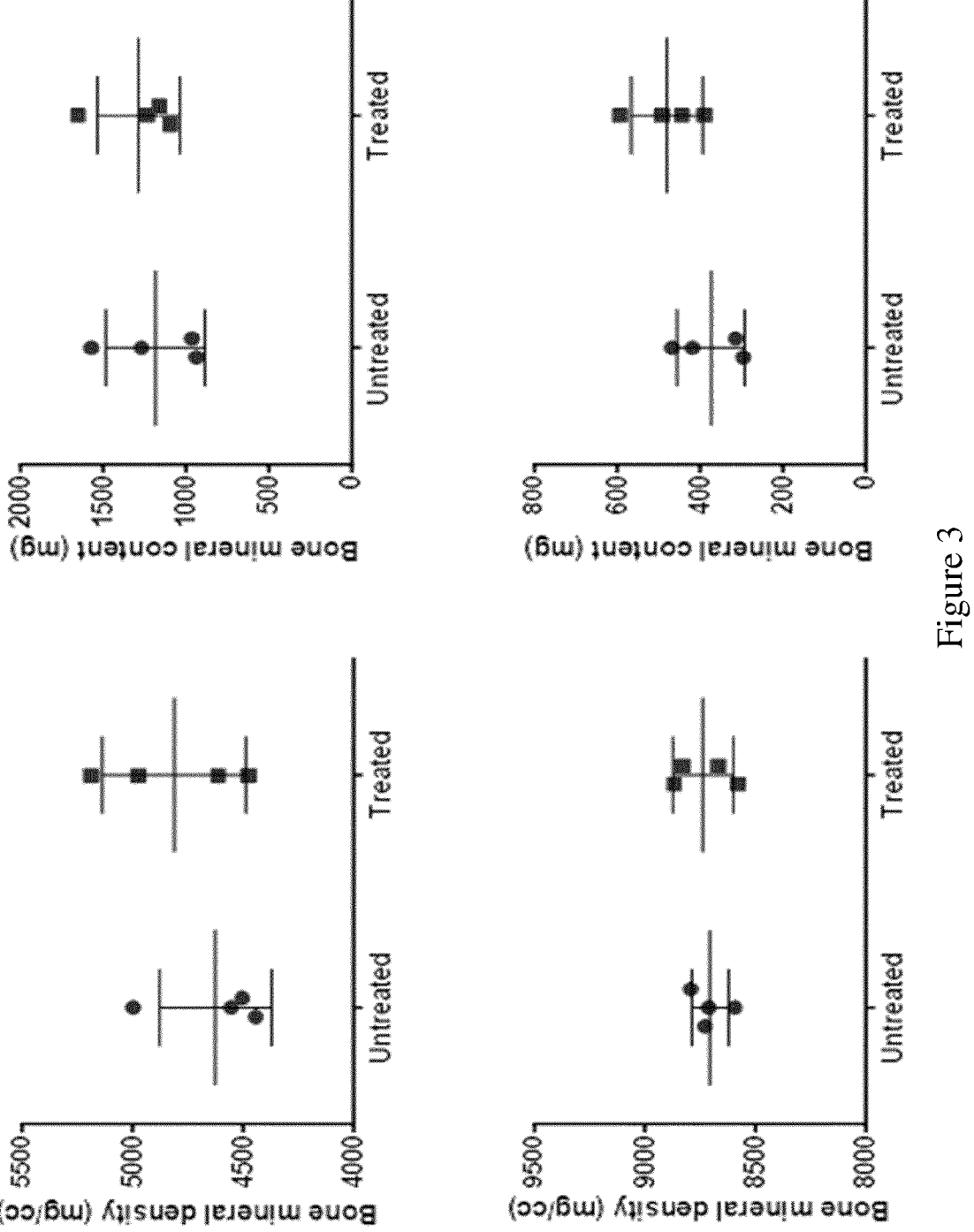
FIG. 3 shows the effect of SH on the bone mineralization after 4 months of treatment as per Example 3: upper panels refer to trabecular region of the bone, while lower panels refer to cortical region.

The status of femurs of adult mice of 24-weeks of age, either treated with SH for 4 months or untreated, was assessed using an X-ray microtomography. The results indicate that after 4 months of treatment with SH there is an improvement in the bone mineral density and content in the trabecular region of the bone, which coincides with an amelioration of the mineral content in the cortical region (FIG. 3).

The improvement of the bones' status was validated also by histological evaluation of the joints, on the animals' knees.

Figure 4:
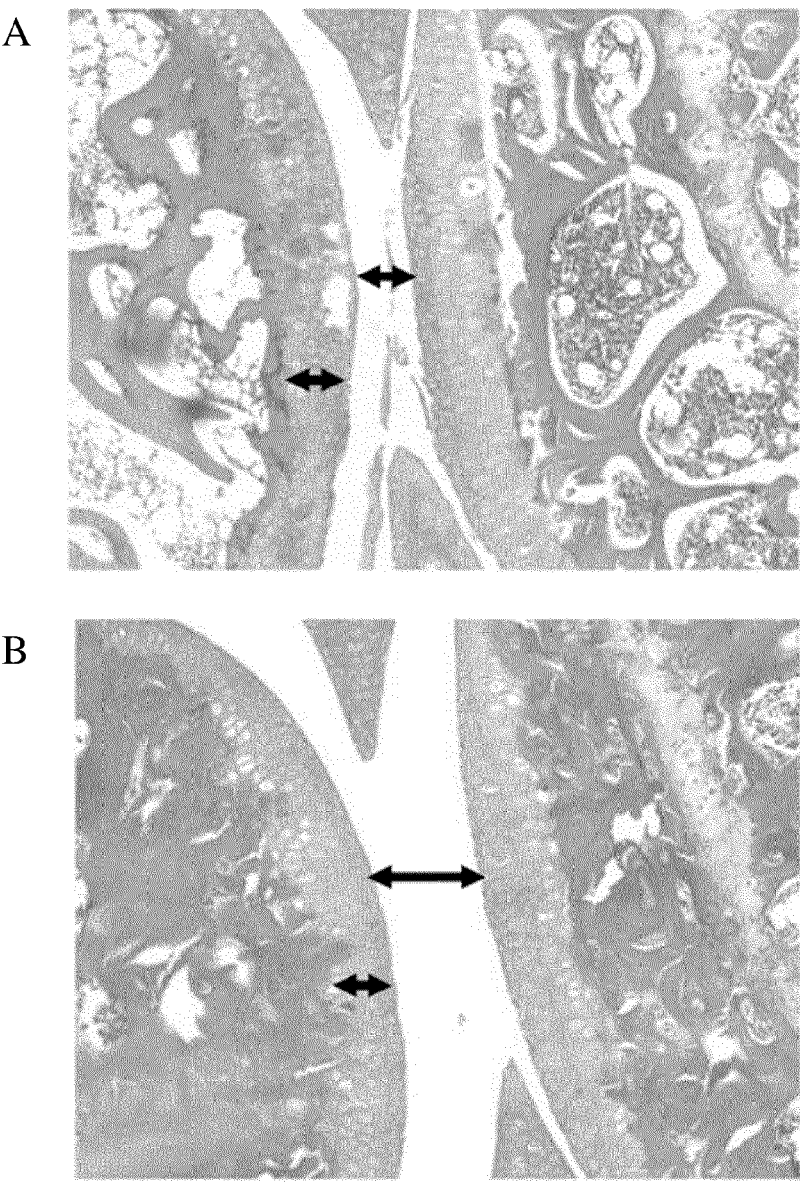
FIG. 4 shows, by hematoxylin/eosin staining, the effect of SH on joints status after 4 months of treatment as per Example 3 (A: untreated; B: SH-treated).
Figure 5:
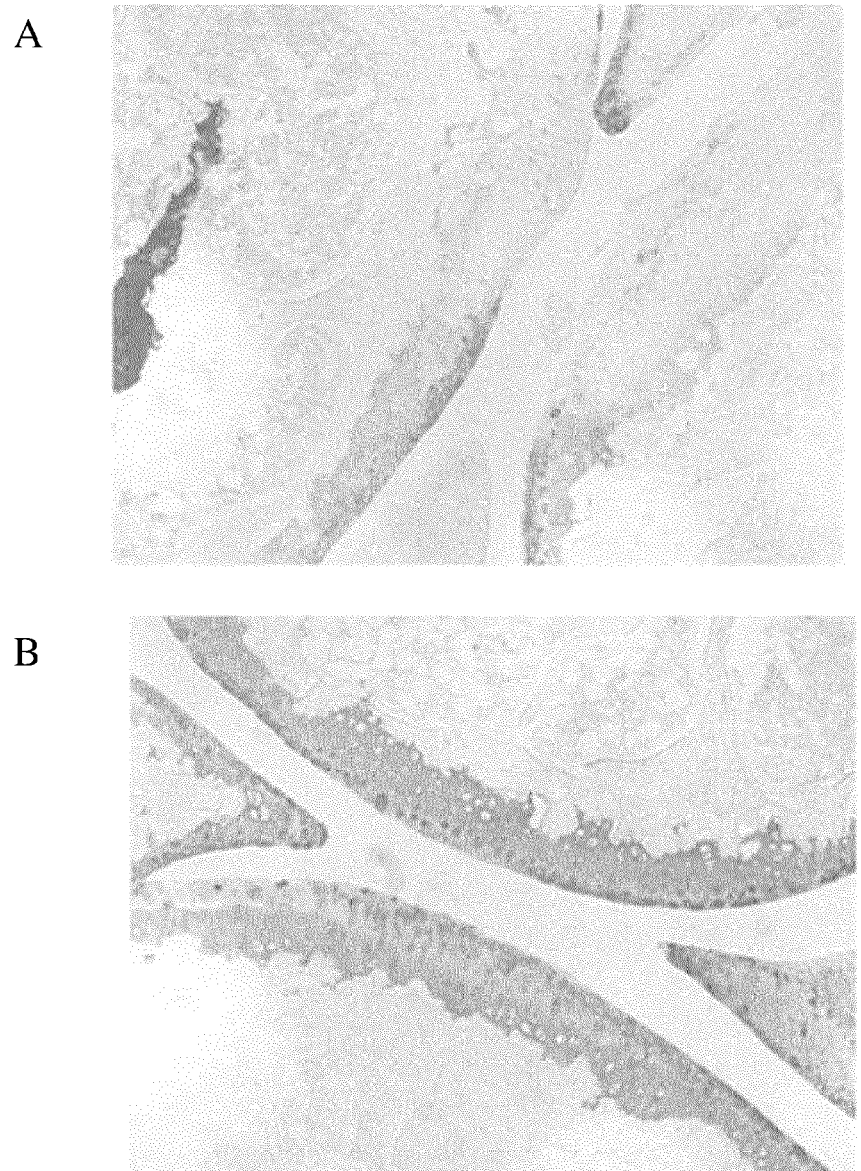
FIG. 5 shows, by toluidine blue staining, the effect of SH on joints status after 4 months of treatment as per Example 3 (A: untreated; B: SH-treated).

Untreated mice presented articulations characterized by a higher damage (FIG. 4A, 5A) compared to mice receiving SH treatment (FIG. 4B, 5B). This was evident both with the haematoxylin/eosin staining (FIG. 4) and with the toluidine blue staining (FIG. 5). Toluidine staining colors proteoglycans and it is specifically used to detect the cartilage condition. The integrity of the proteoglycans' matrix in fact is crucial to maintain the biomechanical properties of the joint cartilage. SH-treated animals joints were more stained than untreated animals' joints.

The invention claimed is:

1. A method of treating a musculoskeletal disorder, said method comprising
   administering to a subject in need thereof a *Salvia haenkei* extract as an active agent, wherein said musculoskeletal disorder is osteoporosis, osteopenia.

2. The method of claim 1, wherein the treatment comprises the improvement in bone density.

3. The method of claim 1, wherein said extract is to be administered via oral route.

4. The method of claim 1, wherein said extract is to be administered in a dose of 1-5000 mg per day.

5. The method of claim 1, wherein the *Salvia haenkei* extract is in the form of a pharmaceutical composition further comprising pharmaceutically acceptable vehicles.

6. The method of claim 1, wherein the *Salvia haenkei* extract is in the form of a food supplement.

7. The method-of claim 5, the pharmaceutical composition being in the form of tablets, capsules, soft gelatin capsules, orodispersible film, lozenges, powder, granulate, liquid solutions, dressing, or suspensions or a combination thereof.

8. The method of claim 6, the food supplement being in the form of tablets, capsules, soft gelatin, capsules, orodispersible film, lozenges, powder, granulate, liquid solutions, dressing, or suspensions or a combination thereof.

9. A method of treating a musculoskeletal disorder, said method comprising
   administering to a subject in need thereof a *Salvia haenkei* extract as an active agent of claim 1, wherein said musculoskeletal disorder is sarcopenia.

10. The method of claim 9, wherein the treatment comprises the improvement in bone density.

11. The method of claim 9, wherein said extract is to be administered via oral route.

12. The method of claim 9, wherein said extract is to be administered in a dose of 1-5000 mg per day.

13. The method of claim 9, wherein the *Salvia haenkei* extract is in the form of a pharmaceutical composition further comprising pharmaceutically acceptable vehicles.

14. The method of claim 9, wherein the *Salvia haenkei* extract is in the form of a food supplement.

15. The method-of claim 13, the pharmaceutical composition being in the form of tablets, capsules, soft gelatin capsules, orodispersible film, lozenges, powder, granulate, liquid solutions, dressing, or suspensions or a combination thereof.

16. The method of claim 14, the food supplement being in the form of tablets, capsules, soft gelatin, capsules, orodispersible film, lozenges, powder, granulate, liquid solutions, dressing, or suspensions or a combination thereof.

* * * * *